United States Patent
Kaupinen et al.

(10) Patent No.: US 11,135,204 B2
(45) Date of Patent: *Oct. 5, 2021

(54) ANHYDROUS COMPOSITIONS OF MTOR INHIBITORS AND METHODS OF USE

(71) Applicant: PALVELLA THERAPEUTICS, INC., Wayne, PA (US)

(72) Inventors: Wesley Harton Kaupinen, Wayne, PA (US); Braham Shroot, Antibes (FR); Simon David Betson, Woking (GB); Charles Rodney Greenaway Evans, Mitcham (GB); Marc Barry Brown, Watford (GB)

(73) Assignee: Palvella Therapeutics, Inc., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/905,059

(22) Filed: Jun. 18, 2020

(65) Prior Publication Data

US 2020/0316034 A1    Oct. 8, 2020

Related U.S. Application Data

(62) Division of application No. 15/863,573, filed on Jan. 5, 2018, now Pat. No. 10,722,499.

(60) Provisional application No. 62/443,117, filed on Jan. 6, 2017.

(51) Int. Cl.

| | | |
|---|---|---|
| *A61K 31/436* | (2006.01) | |
| *A61K 47/10* | (2017.01) | |
| *A61K 47/12* | (2006.01) | |
| *A61P 17/00* | (2006.01) | |
| *A61K 47/32* | (2006.01) | |
| *A61K 47/38* | (2006.01) | |
| *A61K 9/00* | (2006.01) | |
| *A61K 47/14* | (2017.01) | |
| *A61K 47/08* | (2006.01) | |
| *A61K 47/22* | (2006.01) | |
| *A61K 47/28* | (2006.01) | |
| *A61K 47/24* | (2006.01) | |

(52) U.S. Cl.
CPC .......... *A61K 31/436* (2013.01); *A61K 9/0014* (2013.01); *A61K 47/08* (2013.01); *A61K 47/10* (2013.01); *A61K 47/12* (2013.01); *A61K 47/14* (2013.01); *A61K 47/22* (2013.01); *A61K 47/24* (2013.01); *A61K 47/28* (2013.01); *A61K 47/32* (2013.01); *A61K 47/38* (2013.01); *A61P 17/00* (2018.01)

(58) Field of Classification Search
CPC ...... A61K 31/436; A61K 9/0014; A61P 17/00
See application file for complete search history.

(56) References Cited

U.S. PATENT DOCUMENTS

| | | |
|---|---|---|
| 5,286,730 A | 2/1994 | Caufield et al. |
| 5,540,931 A | 7/1996 | Hewitt et al. |
| 5,578,609 A | 11/1996 | Batt et al. |
| 5,631,282 A | 5/1997 | Goetz |
| 5,646,160 A | 7/1997 | Morris et al. |
| 5,670,504 A | 9/1997 | Bochis et al. |
| 5,939,427 A | 8/1999 | Kagayama et al. |
| 5,994,081 A | 11/1999 | Tang et al. |
| 6,110,910 A | 8/2000 | Magolda et al. |
| 6,197,829 B1 | 3/2001 | Fujii et al. |
| 6,221,843 B1 | 4/2001 | Tang et al. |
| 6,352,998 B2 | 3/2002 | Jackman et al. |
| 6,455,518 B2 | 9/2002 | Zenke et al. |
| 6,958,153 B1 | 10/2005 | Ormerod et al. |
| 7,083,802 B2 | 8/2006 | Peyman |
| 7,169,594 B2 | 1/2007 | Guan |
| 7,345,053 B2 | 3/2008 | Garvey |
| 7,416,724 B2 | 8/2008 | Guan |
| 7,534,808 B2 | 5/2009 | Evenou et al. |
| 7,566,718 B2 | 7/2009 | Wong et al. |
| 7,758,886 B2 | 7/2010 | Jauernig et al. |
| 7,763,616 B2 | 7/2010 | Yu et al. |
| 7,776,862 B2 | 8/2010 | McGuinness et al. |
| 7,781,437 B2 | 8/2010 | Kim et al. |
| 7,799,789 B2 | 9/2010 | Anilkumar et al. |
| 7,868,005 B2 | 1/2011 | Rosenblum et al. |
| 7,879,838 B2 | 2/2011 | Zeng et al. |
| 7,985,415 B2 | 7/2011 | Giroux |
| 8,114,385 B2 | 2/2012 | Tamarkin et al. |
| 8,207,170 B2 | 6/2012 | Kim et al. |
| 8,221,752 B2 | 7/2012 | Kasaian et al. |

(Continued)

FOREIGN PATENT DOCUMENTS

| | | |
|---|---|---|
| CA | 2317010 A1 | 7/1999 |
| CA | 2825786 A1 | 8/2012 |

(Continued)

OTHER PUBLICATIONS

Ashton et al. "Prenatal Diagnosis for Inherited Skin Diseases" (2000) Clinics in Dermatology 18:643-648.
Avni et al. "Vertebrate mRNAs with a 5'-Terminal Pyrimidine Tract Are Candidates for Translation Repression in Quiescent Cells: Characterization of the Translation cis-Regulatory Element" (Jun. 1994) Molecular and Cellular Biology 14(6):3822-3833.
Bowden et al. "Mutation of a type II keratin gene (K6a) in pachyonychia congenita" (Jul. 1995) Nat. Genet. 10:363-365 (abstract only).
European Supplemental Search Report and Written Opinion for EP 18736498.9 dated Jul. 17, 2020.
Hay et al. "Upstream and downstream of mTOR" (2004) Genes & Development 18:1926-1945.

(Continued)

*Primary Examiner* — Taina D Matos Negron
(74) *Attorney, Agent, or Firm* — Troutman Pepper Hamilton Sanders LLP

(57) ABSTRACT

Disclosed herein are compositions and methods for topical delivery of mTOR inhibitors. In one embodiment, an anhydrous composition includes one or more mTOR inhibitors, one or more solvents, one or more gelling agents, and one or more antioxidants. Also disclosed herein are methods to treat skin disorders using such compositions.

11 Claims, 4 Drawing Sheets

(56) References Cited

U.S. PATENT DOCUMENTS

| | | | |
|---|---|---|---|
| 8,367,606 B2 | 2/2013 | Tennenbaum et al. |
| 8,372,434 B2 | 2/2013 | Bague et al. |
| 8,435,544 B2 | 5/2013 | Mitra et al. |
| 8,454,945 B2 | 6/2013 | McCook et al. |
| 8,574,562 B2 | 11/2013 | Goebel |
| 8,614,178 B2 | 12/2013 | Theisinger et al. |
| 8,617,598 B2 | 12/2013 | Haeberlin et al. |
| 8,623,833 B2 | 1/2014 | Rothbard et al. |
| 8,663,639 B2 | 3/2014 | Dor et al. |
| 8,715,741 B2 | 5/2014 | Maitra et al. |
| 8,911,786 B2 | 12/2014 | Desai et al. |
| 8,946,256 B2 | 2/2015 | Bacus |
| 9,011,915 B2 | 4/2015 | Wong et al. |
| 9,034,881 B2 | 5/2015 | Magilavy |
| 9,169,269 B2 | 10/2015 | Mangia et al. |
| 9,173,841 B2 | 11/2015 | Kang et al. |
| 9,205,080 B2 | 12/2015 | Kaspar et al. |
| 9,308,262 B2 | 4/2016 | Gunther et al. |
| 9,346,836 B2 | 5/2016 | Morgan |
| 9,360,471 B2 | 6/2016 | Qi |
| 9,447,184 B2 | 9/2016 | Wu et al. |
| 9,522,146 B2 | 12/2016 | Ren et al. |
| 9,526,723 B2 | 12/2016 | Moss et al. |
| 9,549,929 B2 | 1/2017 | Brown et al. |
| 9,549,966 B2 | 1/2017 | Hamrah et al. |
| 9,556,203 B2 | 1/2017 | Cimljanovic et al. |
| 9,757,459 B2 | 9/2017 | Theisinger et al. |
| 9,770,508 B2 | 9/2017 | Gunther et al. |
| 9,855,252 B2 | 1/2018 | Kaspar et al. |
| 10,130,707 B2 | 11/2018 | Gunther et al. |
| 10,172,789 B2 | 1/2019 | Kaspar et al. |
| 10,456,383 B2 | 10/2019 | Teng et al. |
| 2001/0031769 A1 | 10/2001 | Jackman et al. |
| 2002/0015702 A1 | 2/2002 | Burkly et al. |
| 2002/0016625 A1 | 2/2002 | Falotico et al. |
| 2003/0170630 A1 | 9/2003 | Alsobrook et al. |
| 2005/0031547 A1 | 2/2005 | Tamarkin et al. |
| 2005/0090553 A1 | 4/2005 | Shapiro |
| 2005/0192261 A1 | 9/2005 | Jost-Price et al. |
| 2005/0220850 A1* | 10/2005 | Ledergerber ......... A61K 31/445 424/448 |
| 2005/0249757 A1 | 11/2005 | Kannan et al. |
| 2005/0250804 A1 | 11/2005 | Kannan et al. |
| 2005/0250805 A1 | 11/2005 | Kannan et al. |
| 2006/0035907 A1 | 2/2006 | Christensen et al. |
| 2006/0128739 A1 | 6/2006 | Maryanoff et al. |
| 2006/0154952 A1 | 7/2006 | Moore |
| 2006/0194769 A1 | 8/2006 | Johnson et al. |
| 2006/0210604 A1 | 9/2006 | Dadey et al. |
| 2006/0210638 A1 | 9/2006 | Liversidge et al. |
| 2006/0228394 A1 | 10/2006 | Peyman |
| 2006/0264453 A1* | 11/2006 | Mudumba ............... A61K 47/44 514/291 |
| 2007/0031509 A1 | 2/2007 | Sundae |
| 2007/0203171 A1 | 8/2007 | Zhao |
| 2007/0219271 A1 | 9/2007 | Mittmann et al. |
| 2008/0009437 A1 | 1/2008 | Xia et al. |
| 2008/0064668 A1 | 3/2008 | Uskokovic et al. |
| 2008/0124400 A1 | 5/2008 | Liggins et al. |
| 2008/0207670 A1 | 8/2008 | Sirinyan et al. |
| 2008/0207672 A1 | 8/2008 | Kaspar et al. |
| 2008/0299220 A1 | 12/2008 | Tamarkin et al. |
| 2009/0022774 A1 | 1/2009 | Mollison et al. |
| 2009/0088373 A1 | 4/2009 | Gallo et al. |
| 2009/0130029 A1 | 5/2009 | Tamarkin et al. |
| 2009/0226430 A1 | 9/2009 | Hanna et al. |
| 2010/0081681 A1 | 4/2010 | Blagosklonny |
| 2010/0172993 A1 | 7/2010 | Singh et al. |
| 2010/0203103 A1 | 8/2010 | Dana et al. |
| 2012/0022095 A1 | 1/2012 | Teng et al. |
| 2013/0059795 A1 | 3/2013 | Lo et al. |
| 2013/0102572 A1 | 4/2013 | Sugarman |
| 2013/0225630 A1 | 8/2013 | Teng et al. |
| 2013/0225631 A1 | 8/2013 | Teng et al. |
| 2013/0317053 A1 | 11/2013 | Kaneda et al. |
| 2014/0079686 A1 | 3/2014 | Barman et al. |
| 2014/0100180 A1 | 4/2014 | Gunther et al. |
| 2014/0271871 A1 | 9/2014 | Desai et al. |
| 2015/0051242 A1 | 2/2015 | Zhao |
| 2015/0202187 A1 | 7/2015 | Bacus et al. |
| 2015/0238605 A1 | 8/2015 | Gunther et al. |
| 2015/0265582 A1 | 9/2015 | Armer et al. |
| 2015/0328193 A1 | 11/2015 | Henske et al. |
| 2015/0359900 A1 | 12/2015 | Wang et al. |
| 2016/0008471 A1 | 1/2016 | Batt et al. |
| 2016/0024101 A1 | 1/2016 | Elsner et al. |
| 2016/0120860 A1 | 5/2016 | Orlow et al. |
| 2016/0184279 A1 | 6/2016 | Kaspar et al. |
| 2016/0235668 A1 | 8/2016 | Rothberg et al. |
| 2016/0256443 A1 | 9/2016 | Kaspar et al. |
| 2016/0287611 A1 | 10/2016 | Dobak |
| 2016/0326168 A1 | 11/2016 | Ibrahim et al. |
| 2017/0009239 A1 | 1/2017 | Khvorova et al. |
| 2017/0014341 A1 | 1/2017 | Armer et al. |
| 2018/0193320 A1 | 7/2018 | Kaupinen et al. |

FOREIGN PATENT DOCUMENTS

| | | |
|---|---|---|
| CA | 2941436 A1 | 12/2015 |
| EP | 0605161 A2 | 7/1994 |
| EP | 0703985 B1 | 10/2003 |
| EP | 1441696 B1 | 8/2004 |
| EP | 1147766 B1 | 7/2005 |
| EP | 1679064 A2 | 7/2006 |
| EP | 2033968 A1 | 3/2009 |
| EP | 2068932 B1 | 11/2013 |
| EP | 1933759 B1 | 12/2014 |
| EP | 2948134 A1 | 12/2015 |
| WO | 1999024036 A1 | 5/1999 |
| WO | 2000010516 A1 | 3/2000 |
| WO | 2000033877 A1 | 6/2000 |
| WO | WO2000033877 * | 6/2000 |
| WO | 2005091891 A2 | 10/2005 |
| WO | 2006123226 A2 | 11/2006 |
| WO | 2008015539 A2 | 2/2008 |
| WO | 2008063563 A2 | 5/2008 |
| WO | 2009023877 A2 | 2/2009 |
| WO | 2009046436 A1 | 4/2009 |
| WO | 2014117035 A1 | 7/2014 |
| WO | 2014132227 A1 | 9/2014 |
| WO | 2014177123 A1 | 11/2014 |
| WO | 2015121836 A1 | 8/2015 |
| WO | 2016071677 A1 | 5/2016 |
| WO | 2016094732 A1 | 6/2016 |
| WO | 2016124601 A1 | 8/2016 |
| WO | 2017053222 A1 | 3/2017 |
| WO | 2018031789 A1 | 2/2018 |
| WO | 2018129364 A1 | 7/2018 |

OTHER PUBLICATIONS

Hickerson et al. "Rapamycin Selectively Inhibits Expression of an Inducible Keratin (K6a) in Human Keratinocytes and Improves Symptoms in Pachyonychia Congenita Patients" (2009) J. Dermatol. Sci. 56:82-88.

Hickerson et al. "SiRNA-Mediated Selective Inhibition of Mutant Keratin mRNAs Responsible for the Skin Disorder Pachyonychia Congenita" (Oct. 2006) Ann. N. Y. Acad. Sci. 1082:56-61.

International Search Report and Written Opinion for PCT/US2007/024077 dated May 29, 2008.

International Search Report and Written Opinion for PCT/US2014/013066 dated May 7, 2014.

International Search Report and Written Opinion for PCT/US2015/065113 dated Mar. 4, 2016.

International Search Report and Written Opinion for PCT/US2018/012647 dated Mar. 13, 2018.

International Search Report and Written Opinion for PCT/US2019/040283 dated Sep. 19, 2019.

Jefferies et al. "Rapamycin selectively represses translation of the "polypyrimidine tract" mRNA family" (May 1994) PNAS USA 91:4441-4445.

(56) References Cited

OTHER PUBLICATIONS

Jefferies et al. "Rapamycin Suppresses 5'Top Mrna Translation Through Inhibition Of P70s6k" (1997) The EMBO Journal 16(12):3693-3704.

Kaspar et al. "A Regulatory Cis Element and a Specific Binding Factor Involved in the Mitogenic Control of Murine Ribosomal Protein L32 Translation" (Jan. 5, 1992) The Journal of Biological Chemistry and Molecular Biology 267 (1):508-514.

Leigh et al "Keratins (K16 and K17) as markers of keratinocyte hyperproliferation in psoriasis in vivo and in vitro" (Oct. 1995) Br J Dermatology 133:501-511 (abstract only).

Macron "RNAi, startup believes siRNAs can treat extremely rare skin disorder" (Sep. 30, 2005) RNAi News 3 (36):4-5.

Meinert et al. "Clinical Trials Design, Conduct, and Analysis" (1986) Monographs in Epidemiology and Biostatistics , 8th ed. (abstract only).

Ormerod et al. "Treatment of psoriasis with topical sirolimus: preclinical development and a randomized, double-blind trial" (2005) British Journal of Dermatology 152:758-764.

Petroulakis et al. "mTOR signaling: implications for cancer and anticancer therapy" (2006) British Journal of Cancer 94:195-199.

Smith et al. "The Genetic Basis of Pachyonychia Congenita" (2005) J. Invest. Dermatol. Symp. Proc 10:21-30.

Supplemental European Search Report and Written Opinion for EP 14743123 dated Jul. 19, 2016.

Takahashi et al. "Cloning and Characterization of Multiple Human Genes and cDNAs Encoding Highly Related Type II Keratin 6 Isoforms" (Aug. 4, 1995) The Journal of Biological Chemistry 270(31):18581-18592 (NCBI Accession #L42584).

Terada et al. "Rapamycin selectively inhibits translation of mRNAs encoding elongation factors and ribosomal proteins" (Nov. 1994) PNAS USA 91:11477-11481.

Watson et al. "Sirolimus and Everolimus: Inhibitors of Mammalian Target of Rapamycin in Liver Transplantation" (2006) Transplantation Reviews 20:104-114.

Yonezawa "Identification of TOR-interacting Proteins" (Jun. 2003) Mol. Interv. 3(4):189-193.

Zhu "Differential translation of Top mRNA in rapamycin-treated human B lymphocytes" (May 2003) Dept. of Chemistry and Biochemistry, Brigham Young University, Provo, UT, USA (abstract only).

* cited by examiner

ANHYDROUS COMPOSITIONS OF MTOR INHIBITORS AND METHODS OF USE

PRIORITY PARAGRAPH

This application is a divisional of U.S. patent application Ser. No. 15/863,573, filed on Jan. 5, 2018, titled "Anhydrous compositions of mTOR inhibitors and methods of use", which claims priority to the U.S. Provisional Application No. 62/443,117, filed on Jan. 6, 2017, titled "Anhydrous compositions of mTOR inhibitors and methods of use", and each of which is incorporated herein by reference.

SUMMARY

Disclosed herein are compositions and methods for topical delivery of mTOR inhibitors. In one embodiment, an anhydrous composition comprises an effective amount of one or more mTOR inhibitors, one or more solvents, one or more gelling agents, and one or more antioxidants. In some embodiments, the mTOR inhibitor is present from about 0.1 wt % to about 20 wt % of the total composition. In some embodiments, the solvent is present from about 1 wt % to about 99.9 wt % of the total composition. In some embodiments, the gelling agent is present from about 0.1 wt % to about 5 wt % of the total composition. In some embodiments, the antioxidant is present from about 0.001 wt % to about 1 wt % of the total composition.

In additional embodiments, methods of treating a skin disorder in a subject in need thereof comprises topically administering an effective amount of an anhydrous composition comprising an effective amount of one or more mTOR inhibitors, one or more solvents, one or more gelling agents, and one or more antioxidants. In some embodiments, the mTOR inhibitor is present from about 0.1 wt % to about 20 wt % of the total composition. In some embodiments, the solvent is present from about 1 wt % to about 99.9 wt % of the total composition. In some embodiments, the gelling agent is present from about 0.1 wt % to about 5 wt % of the total composition. In some embodiments, the antioxidant is present from about 0.001 wt % to about 1 wt % of the total composition.

DETAILED DESCRIPTION

Figure 1:
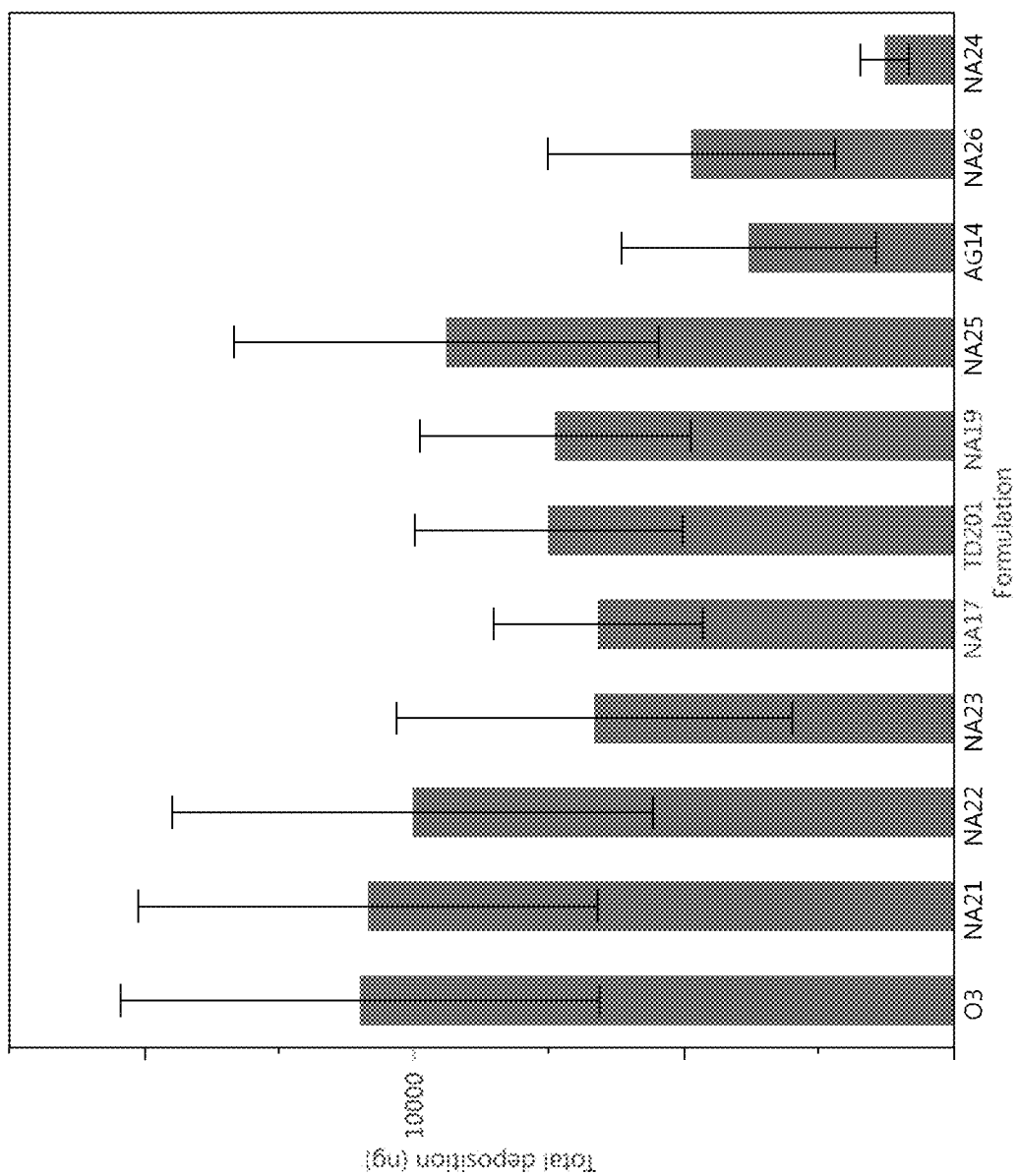
FIG. 1 depicts total mean deposition of rapamycin (ng) in the tissue (combined epidermis and dermis) following application of rapamycin compositions (O3, NA21, NA22, NA23, NA17, NA19, NA25, AG14, NA 26, NA24, TD201). Each error bar is determined using 1 standard deviation from the mean (n=5).

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this application and in the claims, the singular forms "a," "an," and "the" include the plural forms unless the context clearly dictates otherwise. Additionally, the term "includes" means "comprises."

As used herein, all claimed numeric terms are to be read as being preceded by the term, "about," which means plus or minus 10% of the numerical value of the number with which it is being used. Therefore, a claim to "50%" means "about 50%" and encompasses the range of 45%-55%.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

"Administering" when used in conjunction with the mTOR inhibitor means to administer mTOR inhibitor to a patient whereby the mTOR inhibitor positively impacts the tissue to which it is targeted. The mTOR inhibitors described herein can be administered either alone or in combination (concurrently or serially) with other pharmaceutically active agents. For example, the mTOR inhibitors can be administered in combination with other anti-cancer or anti-neoplastic agents, or in combination with other therapies for treating skin disorders. In some embodiments, the mTOR inhibitors described herein can also be administered in combination with (i.e., as a combined composition or as separate compositions) other therapeutics.

An "effective amount" of a composition is a predetermined amount calculated to achieve the desired effect, i.e., to ameliorate, prevent or improve an unwanted condition, disease or symptom of a patient. The activity contemplated by the present methods may include both therapeutic and/or prophylactic treatment, as appropriate. The specific dose of the agent administered according to this invention to obtain therapeutic and/or prophylactic effects will, of course, be determined by the particular circumstances surrounding the case, including, for example, the compound administered, the route of administration, and the condition being treated. The effective amount administered may be determined by a physician in the light of the relevant circumstances including the condition to be treated, the choice of the compound to be administered, and the chosen route of administration.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

The term "disorder" is used in this disclosure to mean, and is used interchangeably with, the terms disease, condition, or illness, unless otherwise indicated.

The weight percentages disclosed herein may be weight-to-weight or weight-to-volume percentages, as appropriate.

Disclosed herein are anhydrous compositions of mTOR inhibitors. In some embodiments, the anhydrous compositions comprise one or more mTOR inhibitors, one or more solvents, one or more gelling agents, and one or more antioxidants.

In some embodiments, the anhydrous composition of mTOR inhibitor has a Cmax of about 120-990 micromolar in the epidermis, and about 36-350 micromolar in the dermis. In some embodiments, the anhydrous composition of mTOR inhibitor has a Tmax of about 15-24 hours in the epidermis. In some embodiments, the anhydrous composition is considered to be bioequivalent or substantially bioequivalent, as measured by accepted topical bioavailability studies, to an anhydrous composition comprising a mTOR inhibitor as described herein.

In some embodiments, the anhydrous composition comprises at least one mTOR inhibitor. Non-limiting examples of mTOR inhibitors are rapamycin (sirolimus), everolimus, pimecrolimus, ridaforolimus, temsirolimus, zotarolimus, rapamycin prodrug AP-23573, AP-23481, torin-1, torin-2, WYE-354, dactolisib, voxtalisib, omipalisib, apitolisib, vistusertib, gedatolisib, WYE-125132, BGT226, palomid 529, GDC-0349, XL388, CZ415, CC-223, ABT-578, SF1126, PKI-587, INK128, AZD8055, NVPBE235, AZD2014, biolimus A9 (umirolimus), GSK2126458, OSI027, PP121, WYE-687, WAY-600, XL765, PI-103, BEZ235, KU-0063794, Torkinib (PP242), PF-04691502, and pharmaceutically acceptable salts, hydrates, solvates, or amorphous solid thereof, and combinations thereof.

In some embodiments, mTOR inhibitors also include specific inhibitors of TOR complex 1, specific inhibitors of TOR complex 2, and the like. In one embodiment, agents that can be used to inhibit TOR complex 2 include but are not limited to small molecules, nucleic acids, proteins, and antibodies. Small molecules include but are not limited to pyridinonequinolines, pyrazolopyrimidines, and pyridopyrimidines. In a further embodiment, small molecules that inhibit TOR complexes 1 and 2 include Torin 1, Torin 2, torkinib (PP242), PP30, KU-0063794, WAY-600, WYE-687, WYE-354, AZD8055, INK128, OS1027, AZD2014, omipalisib, wortmannin, LY294002, PI-103, BGT226, XL765, and NVP-BEZ235. In a further embodiment, the inhibitors include but is not limited to antisense oligonucleotide, siRNA, shRNA, and combinations thereof. In a further embodiment, the agent that inhibits TOR complex 2 would not inhibit TOR complex 1.

In some embodiments, the anhydrous composition may further comprise other compounds regulating mTOR pathway, such as tacrolimus, metformin, and the like.

In some embodiments, the mTOR inhibitor is present from about 0.1 wt % to about 20 wt % of the total composition, about 0.1 wt % to about 15 wt % of the total composition, about 0.1 wt % to about 10 wt % of the total composition, about 0.1 wt % to about 4.5 wt % of the total composition, about 0.1 wt % to about 2 wt % of the total composition, or about 0.1 wt % to about 1 wt % of the total composition, and any individual amount or any ranges between any two of these values. In some embodiments, the weight percentages disclosed herein may be weight-to-weight or weight-to-volume percentages. Non-limiting examples include, about 0.1 wt. %, about 0.5 wt. %, about 0.8 wt. %, about 1 wt. %, about 1.5 wt. %, about 2 wt. %, about 2.5 wt. %, about 3 wt. %, about 3.5 wt. %, about 4 wt. %, about 4.5 wt. %, about 5 wt. %, about 10 wt. %, about 15 wt. %, or about 20 wt. %. In some embodiments, the mTOR inhibitor is rapamycin and is present from about 0.1 wt % to about 10 wt % of the total composition.

In some embodiments, the compounds regulating the mTOR pathway is present from about 0.1 wt % to about 20 wt % of the total composition, about 0.1 wt % to about 15 wt % of the total composition, about 0.1 wt % to about 10 wt % of the total composition, about 0.1 wt % to about 4.5 wt % of the total composition, about 0.1 wt % to about 2 wt % of the total composition, or about 0.1 wt % to about 1 wt % of the total composition, and any individual amount or any ranges between any two of these values. In some embodiments, the weight percentages disclosed herein may be weight-to-weight or weight-to-volume percentages. Non-limiting examples include, about 0.1 wt. %, about 0.5 wt. %, about 1 wt. %, about 1.5 wt. %, about 2 wt. %, about 2.5 wt. %, about 3 wt. %, about 3.5 wt. %, about 4 wt. %, about 4.5 wt. %, about 5 wt. %, about 10 wt. %, about 15 wt. %, or about 20 wt. %.

In some embodiments, the anhydrous compositions may contain one or more solvents that facilitates solubilization of mTOR inhibitors. In some embodiments, solvents include alcohols, polyols, amides, esters, propylene glycol ethers and mixtures thereof. Non-limiting examples of alcohol or polyol include ethanol, isopropanol, butanol, benzyl alcohol, ethylene glycol, propylene glycol, PEG 400, PEG 3350, SR-PEG 400, SR-DMI, oleyl alcohol, castor oil, miglyol 810, liquid paraffin, propylene glycol dicaprylate/dicaprate, butanediols and isomers thereof, glycerol, glycerol triacetate, pentaerythritol, sorbitol, mannitol, Transcutol® P (diethylene glycol monoethyl ether), Transcutol HP, diisopropyl adipate, dimethyl isosorbide, polyethylene glycol, polypropylene glycol, polyvinylalcohol, hydroxypropyl methylcellulose and other cellulose derivatives, cyclodextrins and cyclodextrin derivatives, and mixtures thereof. Examples of amide include 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, polyvinylpyrrolidone, and mixtures thereof. Examples of an ester include ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and mixtures thereof.

In some embodiments, the solvents include benzyl alcohol, DMSO, diglycol, propylene glycol monocaprylate (Capryol 90), diethylene glycol monoethylether (Transcutol®), tetrahydrofurfurylalcohol polyethylene glycol ether (glycofurol), butylene glycol, propylene glycol, diethylene glycol, triethylene glycol, and combinations thereof. More preferably, in some embodiments, solvents include propylene glycol monocaprylate, benzyl alcohol, tetrahydrofurfurylalcohol polyethylene glycol ether, and combinations thereof. In some embodiments, the anhydrous compositions do not contain ethanol. In some embodiments, the anhydrous compositions contain benzyl alcohol less than 10 wt %, less than 8 wt %, less than 6 wt %, less than 4 wt %, or less than 2 wt %. In some embodiments, the anhydrous compositions do not contain benzyl alcohol.

In some embodiments, the solvent is present from about 1 wt % to about 99.9 wt % of the total composition, about 1 wt % to about 90 wt % of the total composition, about 1 wt % to about 80 wt % of the total composition, about 1 wt % to about 70 wt % of the total composition, about 1 wt % to about 60 wt % of the total composition, about 1 wt % to about 50 wt % of the total composition, about 1 wt % to about 40 wt % of the total composition, about 1 wt % to about 30 wt % of the total composition, about 80 wt % to about 99.9 wt % of the total composition, about 85 wt % to about 99.9 wt % of the total composition, about 90 wt % to about 99.9 wt % of the total composition, or about 95 wt % to about 99.9 wt % of the total composition. Non-limiting examples include, about 1 wt. %, about 25 wt. %, about 40 wt. %, about 50 wt. %, about 60 wt. %, about 75 wt. %, about 80 wt. %, about 85 wt. %, about 90 wt. %, about 92 wt. %, about 94 wt. %, about 95 wt. %, about 96 wt. %, about 97 wt. %, about 99 wt. %, or about 99.9 wt. %.

In some embodiments, the anhydrous compositions comprise one or more gelling agents, such as poloxamers and carbomers. Non-limiting examples of poloxamers are poloxamer P-188, poloxamer P-138, poloxamer P-237, poloxamer P-288, poloxamer P-124, poloxamer P-338, and poloxamer P-407. Other block copolymers, such as poly(ethylene glycol/DL lactide Co-glyceride) poly(☐-caprolactum), and hydroxypropyl cellulose (KLUCEL®), glyceryl tris 12-hydroxy stearate, hydroxy stearin, propylene carbonate, polyvinyl pyrolidine can also be used as gelling agents. Non-limiting examples of carbomers that may be used are carbomer 981, carbomer 934, carbomer 934P, carbomer 940, carbomer 941, carbomer 1342, polycarbophil, and calcium polycarbophil. In a preferred embodiment, the gelling agent is selected from hydroxypropyl cellulose, carbomer 981, carbomer 934P, glyceryl tris 12-hydroxy stearate, hydroxy stearin, propylene carbonate, polyvinyl pyrolidine, and combinations thereof. In some embodiments, the gelling agent is present from about 0.1 wt % to about 5 wt % of the total composition, about 0.1 wt % to about 4 wt % of the total composition, about 0.1 wt % to about 3 wt % of the total composition, about 0.1 wt % to about 2 wt % of the total composition, or about 0.1 wt % to about 1 wt % of the total composition.

In some embodiments, the anhydrous compositions comprise one or more antioxidants, such as ascorbic acid, vitamin E and its derivatives, α-tocopherol, ψ-tocopherol, δ-tocopherol, ascorbyl palmitate, propyl gallate (PG), octyl gallate, dodecyl gallate, butylated hydroxy anisole (BHA) and butylated hydroxy toluene (BHT), and D-a-tocopheryl polyethylene glycol 1000 succinate. In some embodiments, the antioxidant is present from about 0.001 wt % to about 1 wt % of the total composition, about 0.001 wt % to about 0.5 wt % of the total composition, about 0.001 wt % to about 0.1 wt % of the total composition, about 0.001 wt % to about 0.05 wt % of the total composition, or about 0.001 wt % to about 0.01 wt % of the total composition.

In some embodiments, the anhydrous composition comprises an effective amount of one or more mTOR inhibitors present from about 0.1 wt % to about 20 wt % of the total composition, one or more solvents present from about 1 wt % to about 99 wt % of the total composition, one or more gelling agents present from about 0.1 wt % to about 5 wt % of the total composition, and one or more antioxidants present from about 0.001 wt. % to about 1 wt. % of the total composition.

In some embodiments, the anhydrous composition comprises an effective amount of one or more mTOR inhibitors present from about 0.1 wt % to about 10 wt % of the total composition, one or more solvents present from about 1 wt % to about 70 wt % of the total composition, and one or more gelling agents present from about 0.1 wt % to about 4 wt % of the total composition, and one or more antioxidants present from about 0.01 wt. % to about 1 wt. %, of the total composition.

In some embodiments, the anhydrous composition comprises an effective amount of one or more mTOR inhibitors present from about 1 wt % to about 10 wt % of the total composition, one or more solvents present from about 10 wt % to about 70 wt % of the total composition, one or more gelling agents present from about 1 wt % to about 5 wt % of the total composition, and one or more antioxidants present from about 0.01 wt. % to about 0.5 wt. % . . . of the total composition.

In some embodiments, the anhydrous composition comprises an effective amount of one or more mTOR inhibitors present from about 1 wt % to about 5 wt % of the total composition, one or more solvents present from about 10 wt % to about 50 wt % of the total composition, one or more gelling agents present from about 1 wt % to about 4 wt % of the total composition, and one or more antioxidants present from about 0.001 wt. % to about 0.01 wt. %. of the total composition.

In some embodiments, the anhydrous compositions comprises an effective amount of one or more mTOR inhibitors, one or more solvents, one or more antioxidants, and no gelling agents.

In some embodiments, the anhydrous compositions of mTOR inhibitor further comprises a polymeric surfactant, a moisturizing agent, a cooling agent, a rheology modifier, a pH adjusting agent, a preservative, and combinations thereof.

In some embodiments, the anhydrous compositions of mTOR inhibitor comprises one or more polymeric surfactants. Polymers having surfactant properties (polymeric surfactant) can be, but are not limited to, hydrophobically modified polyacrylic acid (trade name Pemulen™ TR-I and TR-2), copolymers based on acrylamidoalkyl sulfonic acid and cyclic N-vinylcarboxamides (tradename Aristoflex® AVC), copolymers based on acrylamidoalkyl sulfonic acid and hydrophobically modified methacrylic acid (tradename Aristoflex® HMB), and a homopolymer of acrylamidoalkyl sulfonic acid (tradename Granthix APP). Another class of notable polymeric emulsifier includes hydrophobically-modified, crosslinked, anionic acrylic copolymers, including random polymers, but may also exist in other forms such as block, star, graft, and the like. In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least about 3 carbon atoms. Other materials that may be suitable polymeric surfactants can include ethylene oxide/propylene oxide block copolymers, sold under the trade name PLURONIC®, modified cellulose polymers such as those modified cellulose polymers described by the trade name KLUCEL® (hydroxypropyl cellulose), monomeric anionic surfactants, monomeric amphoteric surfactants, betaine, and combinations thereof. Other suitable polymeric surfactants include copolymers based on acrylamidoalkylsulfonic acids and cyclic N-vinylcarboxamides and/or linear N-vinylcarboxamides (e.g., Aristoflex® AVC and Aristoflex® HMB) and a betaine. In preferred embodiments, the polymeric surfactants include poloxamer P-188, poloxamer P-138, poloxamer P-237, poloxamer P-288, poloxamer P-124, poloxamer P-338, poloxamer P-407, D-a-Tocopheryl polyethylene glycol 1000 succinate, Brij 020, and combinations thereof. In some embodiments, the polymeric surfactant is present from about 0.1 wt % to about 50 wt % of the total composition, about 0.1 wt % to about 40 wt % of the total composition, about 0.1 wt % to about 30 wt % of the total composition, about 0.1 wt % to about 20 wt % of the total composition, or about 0.1 wt % to about 10 wt % of the total composition.

In some embodiments, the anhydrous compositions of mTOR inhibitor may further comprise one or more moisturizing agents or an emollient component, for example mineral oil, dimethicone, cyclomethicone, cholesterol, or combinations thereof. In some embodiments, the anhydrous composition includes liquid emollients such as polyhydric alcohols, polyols, saccharides, triglycerides, hydrocarbons, silicones, fatty acids, fatty, esters, fatty alcohols, and blends thereof. In some embodiments, the moisturizing agent is present from about 0.5 wt % to about 10 wt % of the total composition, about 0.5 wt % to about 8 wt % of the total composition, about 0.5 wt % to about 6 wt % of the total composition, about 0.5 wt % to about 4 wt % of the total composition, or about 0.5 wt % to about 1 wt % of the total composition.

In some embodiments, the anhydrous compositions of mTOR inhibitor comprise one or more cooling agents, such as L-menthol, p-menthane-3,8-diol, isopulegol, menthoxypropane-1,2,-diol, menthyl lactate (such as Frescolat® ML), gingerol, icilin, tea tree oil, methyl salicylate, camphor, peppermint oil, N-ethyl-p-menthane-3-carboxamide, ethyl 3-(p-menthane-3-carboxamido)acetate, 2-isopropyl-N,2,3-trimethylbutyramide, menthone glycerol ketal, menthone glyerine acetal, coolact 10; WS3, WS5, WS23, menthyl glutarate, and mixtures thereof. In some embodiments, the cooling agent is present from about 0.5 wt % to about 10 wt % of the total composition, about 0.5 wt % to about 8 wt % of the total composition, about 0.5 wt % to about 6 wt % of the total composition, about 0.5 wt % to about 4 wt % of the total composition, or about 0.5 wt % to about 2 wt % of the total composition.

In some embodiments, the anhydrous compositions disclosed herein does not contain water. In some embodiments, the anhydrous compositions disclosed herein contains substantially no water. In some embodiments, the anhydrous compositions disclosed herein contain less than 1% of water in the total composition. In some embodiments, the anhydrous compositions disclosed herein contain less than 0.5% of water in the total composition. In some embodiments, the anhydrous compositions disclosed herein contain less than 0.1% of water in the total composition.

In some embodiments, the anhydrous compositions of mTOR inhibitors further comprise a rheology modifier, a pH adjusting agent, a preservative, and combinations thereof.

The compositions of the present invention also can further comprise a polymer having thickening properties (rheology modifier). In one embodiment, the polymer having thickening properties can be a hydrophobically modified cross-linked acrylate copolymer (Carbopol® Ultrez 20). Other polymers having similar properties may also be used. Non-limiting examples of polymers having thickening properties can include PEG-150 distearate, PEG-7 glyceryl cocoate, PEG-200 hydrogenated glyceryl palmitate, PEG-120 methyl glucose dioleate, carboxymethylene polymer, carboxyvinyl polymer, acrylates, C10-C30 alkyl acrylate crosspolymers, isopropyl myristate, and combinations thereof. In some embodiments, the polymer having thickening properties can comprise about 0.1 wt % to about 3 wt %. In another embodiment, polymers having thickening properties can be present in amounts of 0.4 wt % to about 1.0 wt % of the total composition. In one embodiment, the polymer having thickening properties comprises about 0.5 wt % to about 0.75 wt % of the total composition. The thickening polymer can be mixed with the surfactant polymer in some embodiments.

In some embodiments, the compositions of the present invention can further comprise a non-aqueous pH adjusting agent or a non-aqueous buffering agent, which is present in the composition to neutralize and/or activate the thickening polymer in order to facilitate the formation of a composition having the desirable rheological qualities. Any anhydrous base or buffer system known in the art and suitable for use in a skin contact application can be used. In one embodiment, the base can include triethanolamine, tetrasodium ethylenediaminetetraacetic acid (EDTA), alkali metal hydroxides like sodium hydroxide (NaOH), salts of weak acids such as ammonium lactate, sodium citrate, sodium ascorbate, or mixtures thereof. The base component also provides utility in that the pH of the overall composition may be adjusted to a range favorable for minimizing irritation of the skin due to pH effects. In some embodiments compositions of the present invention can also include anhydrous acids or the acid component of a buffer system, and any acid known in the art and appropriate for human skin contact may be used. Examples of acids useful in the present composition and commonly used to adjust pH of topical compositions include but are not limited to: citric acid, lactic acid, ascorbic acid, tartaric acid, and hydrochloric acid, and combinations of these and similar acids. In some embodiments, a phosphate buffer system is used in the compositions. In some embodiments, the composition further comprises a phosphate buffer system and Brij 020. In some embodiments, a phosphate/citrate buffer system is used in the compositions. In some embodiments, the composition contains a phosphate/citrate buffer and Brij 020. Specific examples of the pH levels of the composition include about pH 4, about pH 4.5, about pH 5, about pH 5.6, about pH 6, about pH 7, about pH 7.4, about pH 8, and ranges between any two of these values.

Compositions disclosed herein may further comprise preservatives to prevent the growth of harmful microorganisms. While it is in the aqueous phase that microorganisms tend to grow, microorganisms can also reside in the oil phase. As such, preservatives which have solubility in oil are preferably employed in the present compositions. Generally from one tenth of one percent by weight to one percent by weight of preservatives are adequate. The traditional preservatives for cosmetics and pharmaceuticals are alkyl esters of parahydroxybenzoic acid. Other preservatives which have more recently come into use include hydantoin derivatives, propionate salts, cationic surfactants such as benzalkonium chloride; benzyl alcohol, sorbic acid, and a variety of quaternary ammonium compounds. Cosmetic chemists are familiar with appropriate preservatives and routinely choose them to satisfy the preservative challenge test and to provide product stability. Particularly preferred preservatives for a preferred anhydrous composition of this invention are phenoxyethanol, phenethyl alcohol, methyl and propyl parahydroxybenzoates, imidazolidinyl urea, and quaternium-15. The preservatives should be selected having regard for the use of the composition and possible incompatibilities between the preservatives and the other ingredients in the composition.

In some embodiments, the anhydrous compositions are sustained release compositions for controlled release of mTOR inhibitors in order to diminish rapid uptake and systemic absorption of the applied agent. Sustained (or controlled) release refers to the gradual release of mTOR inhibitors from the composition over a period of time. While there may be an initial burst phase, in some embodiments, it is preferred that the release display relatively linear kinetics, thereby providing a constant supply of the mTOR inhibitor over the release period. The release period may vary from about 1 hour to about 8 hours, depending upon the skin disorder and its intended use. The compositions may further comprise various biodegradable polymers to facilitate slow release, such as poly-lactides (PLA), poly-glycolides (PGA), poly butylene succinate (PBS), polyhydroxyalkanoate (PHA), polycaprolactone acid lactone (PCL), polyhydroxybutyrate (PHB), glycolic amyl (PHV), PHB and PHV copolymer (PHBV), and poly lactic acid (PLA)-polyethylene glycol (PEG) copolymers (PLEG). In some embodiments, the preferred polymer is Pluronic® 127.

In some embodiments, the viscosity of the anhydrous compositions disclosed herein is generally that of a thick liquid or gel but can reach a paste like consistency. Generally, the viscosity is a minimum of about 5,000, 10,000 or 15,000 preferably about 20,000 to a maximum of about 12,000,000, 2,000,000 or even about 600,000 cP.

The anhydrous composition of mTOR inhibitors may comprise further ingredients as required. For example, it may contain a further active ingredient, e.g. a corticosteroid, an antibiotic, an antimycotic, and/or an antiviral agent. Moreover, it may comprise one or more further excipients, such as permeation enhancers (DMSO, Transcutol®, menthol, oleic acid, n-alkanols, 1-alkyl-2-pyrrolidones, N,N-dimethylalkanamides, and 1,2-alkanediols, etc.), and the like.

In some embodiments, the compositions may further comprise other skin care agents, including, but not limited to, retinol, steroids, sunblock, salicylate, minocycline, antifungals, peptides, antibodies, lidocaine, and the like and combinations thereof. In some embodiments, other skin care agents include N-acyl amino acid compounds including, for example, N-acyl phenylalanine, N-acyl tyrosine, and the like, their isomers, including their D and L isomers, salts, derivatives, and mixtures thereof. An example of a suitable N-acyl amino acid is N-undecylenoyl-L-phenylalanine is commercially available under the tradename SEPIWHITE®. Other skin active agents include, but are not limited to, Lavandox, Thallasine 2, Argireline NP, Gatuline In-Tense and Gatuline Expression, Myoxinol LS 9736, Syn-ake, and Instensyl®, Sesaflash™, N-acetyl D-glucosamine, panthenol (for example, DL panthenol available from Alps Pharmaceutical Inc.), tocopheryl nicotinate, benzoyl peroxide, 3-hydroxy benzoic acid, flavonoids (for example, flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (for example, retinyl propionate), phytic acid, N-acetyl-L-cysteine, lipoic acid, tocopherol and its esters (for example, tocopheryl acetate: DL-a-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

One or more sunscreens may be incorporated into the present anhydrous compositions. A variety of sunscreens may be employed including the p-aminobenzoic acid derivatives such as p-(2-ethylhexyl)dimethylaminobenzoate, and benzophenone derivatives such as (2-hydroxy-4-methoxyphenyl)phenylmethanone, Mexoryl™ SX, and Mexoryl™ XL, terephthalylidene dicamphor sulfonic acid, and drometrizole trisiloxane. Other non-limiting examples include benzophenones (oxybenzone and sulisobenzone), cinnamates (octylmethoxy cinnamate and cinoxate), salicylates (homomethyl salicylate) anthranilates, $TiO_2$, avobenzone, bemotrizinol, bisoctrizole, 3-(4-methylbenzylidene)-camphor, cinoxate, diethylamino hydroxybenzoyl hexyl benzoate, dioxybenzone, drometrizole trisiloxane, ecamsule, ethylhexyl triazone, homosalate, menthyl anthranilate, octocrylene, octyl salicylate, iscotrizinol, isopentenyl-4-methoxycinnamate, octyl-dimethyl-p-aminobenzoic acid, octyl-methoxycinnamate, oxybenzone, polysilicone-15, trolamine salicylate, and ZnO. The exact amount of sunscreen employed in the present compositions will vary depending on the degree of protection desired from the sun's harmful rays.

The anhydrous compositions of the invention may also comprise one or more pigments to color the composition, and a fragrance, such as Firmenich and Co. 66.001/NY/G fragrance oil, to make the composition soothing to the olfactory system. The amount of these ingredients present in the composition will depend on the specific effect desired.

In embodiments, the anhydrous compositions may be in solid dosage forms including, but not limited to, topical dosage forms including, but not limited to, solutions, powders, fluid suspensions, semi-solids, ointments, pastes, creams, lotions, gels, jellies, and foams; and parenteral dosage forms including, but not limited to, solutions, suspensions, and dry powders. The active ingredients can be contained in such compositions with pharmaceutically acceptable diluents, fillers, disintegrants, binders, lubricants, surfactants, hydrophobic vehicles, emulsifiers, buffers, humectants, moisturizers, solubilizers, preservatives and the like. Pharmaceutical compositions of the compounds also can include suitable solid or gel phase carriers or excipients. Examples of such carriers or excipients include but are not limited to calcium carbonate, calcium phosphate, gelatin, and polymers such as, for example, polyethylene glycols.

In some embodiments, the anhydrous compositions disclosed herein may be in the form of a paste, a liquid, lotion, spray, aerosol, powder, ointment, cream, mouthwash, toothpaste, foam, gel, a solid stick, and combinations thereof. In some embodiments, the compositions disclosed herein are easy to spread, quick absorption, moisturising, non-greasy, non-irritating to patients' skin, aesthetically pleasing to use, and has cooling effect.

In embodiments, the compositions described herein may be formulated as a liquid. Liquid dosage forms for topical administration may include diluents such as, for example, alcohols, glycols, oils, and the like. Such compositions may also include wetting agents or emulsifiers. In some embodiments, the compositions of embodiments may be formulated as oil-in-water or water-in-oil emulsion. A cream can be a water-in-oil (w/o) emulsion in which an aqueous phase is dispersed in an oil phase, or an oil-in-water (o/w) emulsion in which an oil is dispersed within an aqueous base. An ointment generally refers to a more viscous oil-in-water cream. Traditional ointment bases (i.e. carrier) include hydrocarbons (petrolatum, beeswax, etc.) vegetable oils, fatty alcohols (cholesterol, lanoilin, wool alcohol, stearyl alcohol, etc.) or silicones. Insoluble solids such as starch, zinc oxide, calcium carbonate, or talc can also be used in ointments and creams. Gel forms of the compositions described above can be formed by the entrapment of large amounts of aqueous or aqueous-alcoholic liquids in a network of polymers or of colloidal solid particles. Such polymers or colloids (gelling or thickening agents) are typically present at concentrations of less than 10% w/w and include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, and the like.

In some embodiments, the mTOR inhibitors in the compositions disclosed herein are stable for extended periods of time. For example, in some embodiments, the mTOR inhibitors in the compositions are stable at temperature ranges from about 4° C. to about 50° C. for a period of 12-36 months. In some embodiments, the mTOR inhibitors in the compositions are stable at temperature ranges from about 4° C. to about 45° C. for a period of 12-36 months. In some embodiments, the mTOR inhibitors in the compositions are stable at temperature ranges from about 4° C. to about 40° C. for a period of 12-36 months. In some embodiments, the mTOR inhibitors in the compositions are stable at temperature ranges from about 4° C. to about 35° C. for a period of 12-36 months. in some embodiments, the mTOR inhibitors in the compositions are stable at temperature ranges from about 4° C. to about 30° C. for a period of 12-36 months.

Also disclosed herein are methods to treat a skin disorder in a subject. In some embodiments, a method of treating a skin disorder in a subject comprises topically administering an effective amount of an anhydrous composition comprising an effective amount of one or more mTOR inhibitors, one or more solvents, one or more gelling agents, and one or more antioxidants.

In some embodiments, a method of treating a skin disorder in a subject comprises topically administering an effective amount of an anhydrous composition comprising an effective amount of one or more mTOR inhibitors, one or more solvents, and one or more antioxidants.

Non-limiting examples of skin disorder that may be treated by the anhydrous compositions include plantar hyperkeratosis, blisters, tuberous sclerosis, seborrheic keratosis, keratosis pilaris, epidermolysis bullosa, multiple minute digitate hyperkeratosis, hyperkeratosis lenticularis perstans, stasis dermatitis, focal acral hyperkeratosis, follicular hyperkeratosis, lichenoid keratoses (lichen planus, lichen sclerosus), chronic erosive oral lichen, Conradi-Eltinermann, epidermolytic ichthyosis, erythrokeratoderma variabilis, ichthyosis hystrix, KID syndrome, Netherton syndrome, Olmsted syndrome, Refsum disease, Sjogren-Larsson Syndrome, actinic keratosis, pachyonychia congenita, hyperhidrosis, warts, calluses, dermatitis (contact dermatitis, drug-induced dermatitis, allergic dermatitis, nummular dermatitis, perioral dermatitis, neurodermatitis, seborrheic dermatitis, and atopic dermatitis), psoriasis, acne, carbunculosis, cellulitis, furunculosis, granuloma, acanthosis nigricans, athlete's foot, bacterial vaginosis, balanitis, dermatofibrosarcoma protruberans, basal cell carcinoma, squamous cell carcinoma, melanoma, merkel cell carcinoma, keloid, cystic lymphangioma, Cavernous lymphangioma, venous malformation, epidermal nevi, bromhidrosis, dermatophytosis, candidiasis, onychomycosis, tinea (tinea alba, tinea pedis, tinea unguium, tinea manuum, tinea cruris, tinea corporis, tinea capitis, tinea faciei, tinea barbae, tinea imbricata, tinea nigra, tinea versicolor, tinea incognito), eczema, dyshydrotic eczema, decubitous ulcer, ecthyma, erysipalus, erythema multiforme, impetigo, insect bites, genital warts, hemangioma, herpes, hives, hyperhidrosis, filariasis, lentigines, lupus, miliaria, milker's nodules, molluscum contagiosum, myiasis, scabies, cutaneous larva migrans, furuncular myiasis, migratory myiasis, pediculosis, nevus araneus, panniculitis, paronychia, pemphigoid, pityriasis, pruritis vulvae, rosacea, trichomoniasis, vaginal yeast infection, vitiligo, xeroderma, angiofibroma, Bannayan-Riley-Ruvalcaba syndrome, basal cell nevus syndrome, Birt-Hogg-Dube syndrome, Blue rubber bleb nevus syndrome, Cowden disease, cutaneous T-cell lymphoma, diffuse microcystic lymphatic malformations, epidermolysis bullosa simplex, extramammary paget, familial multiple discoid fibromas, Hailey-Hailey disease, infantile hemangiomas, juvenile polyposis syndrome, Kaposi sarcoma, Kaposiform hemangioendothelioma, Keloid scar disease, Lhermitte-Duclos syndrome, metastatic melanoma, Muir-Torre syndrome, neurofibromatosis, nonmelanoma skin cancer, oral graft-versus-host disease, Pemphigus vulgaris, Peutz-Jeghers syndrome, Port-wine stains, Proteus syndrome, Proteus-like Syndrome, refractory hemangioendotheliomas in Maffucci syndrome, Sturge-weber syndrome, hereditary footpad hyperkeratosis (HFH) in canines, cutaneous sarcoidosis, cutaneous Castleman Disease, Bullous Pemphigoid, and combinations thereof.

In some embodiments, the skin disorder that is treated is angiofibroma. In some embodiments, the skin disorder that is treated is pachyonychia congenita. In some embodiments, a symptom of pachyonychia congenita is treated and the symptom is selected from pain, itch or a combination thereof.

In some embodiments, administration of the composition is by topical application.

In some embodiments, the anhydrous composition of mTOR inhibitors are administered topically, and the mTOR inhibitor reaches epidermal and dermal layer through absorption. In some embodiments, the topical application of the anhydrous composition does not result in systemic absorption of the mTOR inhibitors.

In some embodiments, the topical administration of the anhydrous compositions results in delivery of the mTOR inhibitors to epidermis of the skin. In some embodiments, the topical administration of the anhydrous compositions results in delivery of mTOR inhibitors to epidermis and dermis.

In some embodiments, the method of treating a skin disorder involves administering topically an anhydrous composition that includes one or more mTOR inhibitors present from about 0.1 wt % to about 20 wt % of the total composition, one or more solvents present from about 1 wt % to about 99 wt % of the total composition, one or more gelling agents present from about 0.1 wt % to about 5 wt % of the total composition, and one or more antioxidants present from about 0.001 wt % to about 1 wt % of the total composition. In some embodiments, the composition may further include a polymeric surfactant, a moisturizing agent, a cooling agent, a rheology modifier, a pH adjusting agent, a preservative, and combinations thereof. In some embodiments, the anhydrous compositions do not contain gelling agents.

In some embodiments, the anhydrous compositions can be topically applied to the skin, preferably by manually rubbing the applied amount over the skin to thoroughly coat the skin. The rubbing action preferably is a gentle rubbing or massaging for a period of at least about 5 second, preferably about 5 to about 30 seconds to spread all over the skin. The moisture or water present on the skin may emulsify the anhydrous composition due to continuous rubbing and massaging, resulting in the formation of an emulsion in situ on the skin.

Some embodiments of the invention are directed to a method of treating hair loss in a subject. In some embodiments, the method of treating hair loss includes administering to the subject in need thereof an effective amount of an anhydrous composition comprising an effective amount one or more mTOR inhibitors, one or more solvents, one or more gelling agents, and one or more antioxidants. In embodiments, treatment of diseases related to hair, hair shaft, hair follicles, hair bulbs, oil glands, and components thereof, include, for example, hair loss, dandruff, seborrheic dermatitis, alopecia areata, hair disease, ringworm, tinea capitis, folliculitis, pattern hair loss, telogen effluvium, cradle cap, trichotillomania, traction alopecia, trichorrhexis nodosa, folliculitis decalvans, head lice infestation, frontal fibrosing alopecia, non-scarring hair loss, pityriasis amiantacea, dissecting cellulitis of the scalp, acne keloidalis nuchae, monilethrix, pediculosis, alopecia totalis, pseudopelade of Brocq, bubble hair deformity, hair casts, hypertrichosis, ingrown hair, monilethrix, premature greying of hair, pattern hair loss, trichorrhexis invaginata, and the like.

The compositions disclosed herein may be applied topically to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal. Other actions that make their concept appearance are concurrent skin benefits in addition to hair reduction. The composition can also be applied to the legs, arms, torso or armpits. The composition is suitable, for example, for reducing the growth of unwanted hair in women. In humans, the composition may be applied once or twice a day, or even more frequently, to achieve a perceived reduction in hair growth. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Some embodiments of the invention are directed to a method of treating dry eye syndrome in a subject. In some embodiments, the method of treating dry eye syndrome includes administering to the subject in need thereof an effective amount of an anhydrous composition comprising one or more mTOR inhibitors, one or more solvents, one or more gelling agents, and one or more antioxidants.

In some embodiments, the anhydrous compositions of the present invention can, for example, be applied to a plaster, patch, bandage, or a film. In some embodiments, topical delivery is aided by the use of ultrasound technology. The ultrasound energy is applied over the tissue and to assist the diffusion of the composition past the tissue.

In embodiments, the compositions disclosed herein can be in the form of transdermal patches. The transdermal patches can be in any conventional form such as, for example, a strip, a gauze, a film, and the like. Patch material may be nonwoven or woven (e.g., gauze dressing). Layers may also be laminated during processing. It may be nonocclusive or occlusive, but the latter is preferred for backing layers. The patch is preferably hermetically sealed for storage (e.g., foil packaging). The patch can be held onto the skin and components of the patch can be held together using various adhesives. For example, the transdermal patch can be in the form of a band-aid type device, or it may be packaged in a small metal or plastic "cup", which is strapped onto the appropriate site using an adhesive, tape, or an outer fabric or leather strap, similar to that worn as part of a watch. The entire patch may be disposable or may be refillable. In some embodiments, the compositions disclosed herein can be coated on bandages, mixed with bioadhesives, or included in dressings.

In some embodiments, a hand pump may be used to dispense the mTOR inhibitor anhydrous compositions. For example, the hand pump may be configured to dispense the required dose of mTOR inhibitor within a tolerance specified by a corresponding label approved by a government regulatory agency. The hand pump may deliver 0.5-10 mL of the composition per pump action, such as 1, 2, 3, 4, or 5 mL of the composition per pump action. In some embodiments, the mTOR inhibitor compositions may be packaged along with a pharmaceutically acceptable hand pump.

In some embodiments, the anhydrous compositions may be administered in a conventional manner by any route by which they retain activity. For example, the anhydrous composition of mTOR inhibitors may be administered by routes including, but not limited to, topical, transdermal, or percutaneous. Thus, modes of administration for the compounds (either alone or in combination with other pharmaceuticals) can be, but are not limited to, sublingual, or by use of vaginal creams, suppositories, pessaries, vaginal rings, rectal suppositories, and percutaneous and topical forms such as patches and creams, lotions, gels.

The particular quantity of composition administered, of course, will be determined by the particular circumstances surrounding its use, including the composition administered, the condition of the skin, the age of the user, the degree of the skin disorder, and similar considerations. For example, the dosage may depend on the particular animal treated, the age, weight, and health of the subject, the types of concurrent treatment, if any, and frequency of treatments. Many of these factors can be easily determined by one of skill in the art (e.g., by the clinician). Typically, a single application of the composition will be applied topically to cover adequately the affected area of the skin. Subsequent applications may be made as needed to deliver the desired level of mTOR inhibitors.

In some embodiments, the composition can be administered one, two, three, four, five or more times each day, and applying can be carried out for a period of at least 1 month, 2 months, 3 months, 4 months, 6 months, 8 months or 12 months.

In some embodiments, the composition may be administered once, as needed, once daily, twice daily, three times a day, once a week, twice a week, every other week, every other day, or the like for one or more dosing cycles. A dosing cycle may include administration for about 1 week, about 2 weeks, about 3 weeks, about 4 weeks, about 5 weeks, about 6 weeks, about 7 weeks, about 8 weeks, about 9 weeks, or about 10 weeks. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks.

In embodiments, the method of treating a skin disorder comprising administering the anhydrous composition described herein, wherein the method does not further include any additional medical or therapeutic intervention for treatment of the skin disorder.

In embodiments, the method of treating a skin disorder comprises administering the anhydrous compositions described herein, wherein the mTOR inhibitor is the only active agent administered for treating the skin disorder.

In some embodiments, the methods may include a variety of additional steps including, for example, cleaning the surface tissue at the site of applying and the like.

In embodiments, the methods may further include descaling or debriding of the tissue surface before, during or after administration of the compositions described herein. In embodiments, methods for descaling or debriding tissue surface may include electromagnetic radiation, laser, dermal abrasion, chemical peel, ultrasound, heating, cooling, or by a needle.

In embodiments, the tissue surface is descaled or debrided with abrasion. Abrasion of the outer layer or epidermis of the skin (dermal abrasion) is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

In embodiments, the tissue surface is descaled or debrided with microdermabrasion. Microdermabrasion refers generally to a procedure in which the surface of the skin is removed due to mechanical rubbing by a handpiece emitting a stream of sand or grit. For example, a handpiece can be used to direct an air flow containing tiny crystals of aluminum oxide, sodium chloride, or sodium bicarbonate. The momentum of the grit tends to wear away two to three cell layers of the skin with each pass of the handpiece. Alternatively, new "crystal-free" microdermabrasion techniques utilize a diamond-tipped handpiece without a stream of grit.

In embodiments, the tissue surface is descaled or debrided with electromagnetic radiation, for instance using a so-called fractional laser treatment. By way of example, such methods employ electromagnetic radiation (EMR) having one or more wavelengths of between approximately 1,850 to 100,000 nanometers and with pulse widths of between approximately 1 femtosecond (1×10-15 s) to 10 milliseconds (10×10-3 s) with fluence in the range of from approximately 1 J/cm2 to 300 J/cm2. In other examples, the tissue is descaled or debrided with electromagnetic radiation having one or more wavelengths of between approximately 2,200 to 5,000 nanometers. In still other examples, the tissue is descaled or debrided with electromagnetic radiation having one or more wavelengths of between approximately 190 to 320 nanometers with fluence in the range of from 1 J/cm2 to 300 J/cm2. Optionally, conditions selected for debriding portions of the tissue minimize the coagulation zone of tissue damage, for instance by keeping the coagulation zone to a relatively small diameter surrounding the ablated void.

Electromagnetic radiation (EMR), particularly in the form of laser light or other optical radiation, has been used in a variety of cosmetic and medical applications, including uses in dermatology, dentistry, ophthalmology, gynecology, otorhinolaryngology and internal medicine. For most dermatological applications, EMR treatment can be performed with a device that delivers the EMR to the surface of the targeted tissue(s). EMR treatment is typically designed to (a) deliver one or more particular wavelengths (or a particular continuous range of wavelengths) of energy to a tissue to induce a particular chemical reaction, (b) deliver energy to a tissue to cause an increase in temperature, or (c) deliver energy to a tissue to damage or destroy cellular or extracellular structures, such as for skin remodeling. Examples of devices that have been used to treat the skin during cosmetic procedures such as skin rejuvenation include the Palomar® LuxIR, the Palomar® 1540, 1440 and 2940 Fractional Handpieces, the Reliant Fraxel® SR Laser and similar devices by Lumenis, Alma Lasers, Sciton and many others.

In embodiments, the methods may further include photodynamic therapy before, during or after administration of the compositions described herein. Photodynamic therapy is a minimally invasive two-step medical procedure that uses photoactivatable drugs called photosensitizers to treat a range of diseases. First, a photosensitizer is administered and, once it has permeated the target tissue, the photosensitizer is then activated by exposure to a dose of electromagnetic (usually light) radiation at a particular wavelength. The compositions disclosed herein may contain a photosensitizer. In embodiments, any suitable photosensitizing agent or mixture of agents may be used herein. Generally, these will absorb radiation in the range of from about 380 nm to about 900 nm. As used herein, "photosensitizer" or "photosensitizing agent" preferably means a chemical compound which, when contacted by radiation of a certain wavelength, forms singlet oxygen or thermal energy. Non-limiting examples of photosensitizers include aminolevulinic acid esters, porphyrins, porphyrin derivatives, bacteriochlorins, isobacteriochlorins, phthalocyanine, naphthalocyanines, pyropheophorbides, sapphyrins, texaphyrins, tetrahydrochlorins, purpurins, porphycenes, phenothiaziniums, and metal complexes such as, but not limited to, tin, aluminum, zinc, lutetium, and tin ethyl etiopurpurin (SnET2), and combinations thereof.

The compositions of the present invention can also be administered in combination with other active ingredients, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLES

Example 1

An exemplary anhydrous composition is described below:

| Component | wt % | Role |
|---|---|---|
| tetrahydrofurfurylalcohol polyethylene glycol ether | 34.55% | drug solvent |
| Transcutol ® | 15% | co-solvent |
| propylene glycol monocaprylate | 20% | co-solvent |
| Propylene Glycol | 5% | skin penetration enhancer/solvent |
| Poloxamer 407 | 10% | surfactant |
| WS5 | 1.05% | cooling agent |
| rapamycin | 1.2% | API |
| cholesterol | 0.95% | emollient |
| Silicones | 10% | emollient |
| Klucel ® | 2.25% | gelling agent |

Example 2

An exemplary anhydrous composition is described below:

| Component | wt % | Role |
|---|---|---|
| tetrahydrofurfurylalcohol polyethylene glycol ether | 29.42% | drug solvent |
| Transcutol ® | 9% | co-solvent |
| PEG400 | 35% | co-solvent |
| Propylene Glycol | 5% | skin penetration enhancer/solvent |
| WS5 | 1.05% | cooling agent |
| rapamycin | 2.4% | API |
| Cholesterol | 0.90% | emollient |
| Cyclomethicone | 10% | emollient |
| Dimethicone | 5% | emollient |
| Klucel ® | 2.23% | gelling agent |

Example 3

An exemplary anhydrous composition is described below:

| Component | wt % | Role |
|---|---|---|
| Capryilic/Capric Triclycerides | 30.45% | drug solvent |
| Transcutol | 10% | co-solvent |
| Glycofural | 25% | co-solvent |
| Propylene Glycol | 5% | skin penetration enhancer/solvent |
| Isopropyl myristate | 8% | emollient/thickening agent |
| WS5 | 1.05% | cooling agent |
| rapamycin | 2.2% | API |
| Ascorbyl Palmitate | 0.3% | antioxidant |
| Cyclomethicone | 10% | emollient |
| Dimethicone | 5% | emollient |
| Carbopol | 3% | gelling agent |

Example 4

An exemplary anhydrous composition (NA 17) is described below:

| component | Wt % | Role |
|---|---|---|
| Rapamycin | 3.26 | API |
| Isopropyl alcohol | 15 | solvent |
| PEG400 | 55.668 | solvent |
| Transcutol P | 15 | penetration enhancer/solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 5

An exemplary anhydrous composition (NA 19) is described below:

| component | Wt % | Role |
|---|---|---|
| Rapamycin | 3.26 | API |
| Isopropyl alcohol | 15 | solvent |
| PEG400 | 55.388 | solvent |
| Transcutol P | 15 | penetration enhancer/solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |
| peppermint oil | 0.2 | cooling agent |
| menthol | 0.08 | cooling agent |

Example 6

An exemplary anhydrous composition (NA 21) is described below:

| component | Wt % | Role |
|---|---|---|
| Rapamycin | 4.54 | API |
| Isopropyl alcohol | 15 | solvent |
| PEG400 | 44.388 | solvent |
| Transcutol P | 25 | penetration enhancer/solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 7

An exemplary anhydrous composition (NA 22) is described below:

| component | Wt % | Role |
|---|---|---|
| Rapamycin | 3.9 | API |
| Isopropyl alcohol | 15 | solvent |
| PEG400 | 55.3 | solvent |

-continued

| component | Wt % | Role |
|---|---|---|
| diisopropyl adipate | 15 | solvent |
| Glycerol | 10 | solvent |
| Klucel ® | 0.75 | gelling agent |
| Propyl gallate | 0.05 | antioxidant |
| Ascorbyl palmitate | 0.02 | antioxidant |
| a-tocopherol | 0.002 | antioxidant |

Example 8

An exemplary anhydrous composition (NA 23) is described below:

| component | Wt % | Role |
|---|---|---|
| Rapamycin | 4.51 | API |
| ethanol | 15 | solvent |
| PEG400 | 54.418 | solvent |
| diisopropyl adipate | 15 | solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 9

An exemplary anhydrous composition (NA 24) is described below:

| component | Wt % | Role |
|---|---|---|
| Rapamycin | 2.384 | API |
| Isopropyl alcohol | 15 | solvent |
| PEG400 | 56.548 | solvent |
| Propylene glycol | 15 | penetration enhancer/solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 10

An exemplary anhydrous composition (NA 25) is described below:

| component | Wt % | Role |
|---|---|---|
| Rapamycin | 2.69 | API |
| Isopropyl alcohol | 15 | solvent |
| PEG400 | 26.238 | solvent |
| Propylene glycol | 15 | penetration enhancer/solvent |
| Transcutol P | 25 | penetration enhancer/solvent |
| Diisopropyl adipate | 15 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 11

An exemplary anhydrous composition (NA 26) is described below:

| component | Wt % | Role |
|---|---|---|
| Rapamycin | 3.254 | API |
| Isopropyl alcohol | 15 | solvent |
| PEG400 | 47.608 | solvent |
| Propylene glycol | 15 | penetration enhancer/solvent |
| Transcutol P | 10 | penetration enhancer/solvent |
| Glycerol | 10 | solvent |
| Klucel ® | 1 | gelling agent |
| Propyl gallate | 0.05 | antioxidant |
| Ascorbyl palmitate | 0.02 | antioxidant |
| a-tocopherol | 0.002 | antioxidant |

Example 12

An exemplary ointment composition (O3) is described below:

| component | Wt % | Role |
|---|---|---|
| Rapamycin | 4.59 | API |
| PEG400 | 34.34 | solvent |
| Transcutol P | 47.998 | penetration enhancer/solvent |
| PEG 3350 | 13 | solvent |
| Propyl gallate | 0.05 | antioxidant |
| Ascorbyl palmitate | 0.02 | antioxidant |
| a-tocopherol | 0.002 | antioxidant |

Example 13

An exemplary aqueous composition (TD201) is described below:

| component | Wt % |
|---|---|
| Rapamycin | 1 |
| water | 87.95 |
| Pemulen TR-1 | 0.28 |
| Carbopol Ultrez 10 | 0.76 |
| Propylene glycol | 2.87 |
| Oleic acid | 1.43 |
| Mineral oil | 0.95 |
| Triethanol amine (q.s to pH 5-7) | ca. 0.76 |
| Benzyl alcohol | 4 |

Example 14

An exemplary anhydrous composition (NA 28) is described below:

| component | Wt % | Role |
|---|---|---|
| Rapamycin | 3.9 | API |
| Isopropyl alcohol | 15 | solvent |
| PEG400 | 51 | solvent |
| Propylene glycol | 1.5 | penetration enhancer/solvent |

| component | Wt % | Role |
| --- | --- | --- |
| Diisopropyl adipate | 15 | solvent |
| Glycerol | 10 | solvent |
| Benzyl alcohol | 2 | solvent |
| Oleyl alcohol | 0.75 | solvent |
| Klucel ® | 0.75 | gelling agent |
| Propyl gallate | 0.05 | antioxidant |
| Ascorbyl palmitate | 0.02 | antioxidant |
| a-tocopherol | 0.002 | antioxidant |

Example 15

An exemplary anhydrous composition (NA 33) is described below:

| component | Wt % | Role |
| --- | --- | --- |
| Rapamycin | 3.9 | API |
| PEG400 | 28.3 | solvent |
| Propylene glycol | 15 | penetration enhancer/solvent |
| Transcutol P | 15 | Penetration enhancer/solvent |
| Diisopropyl adipate | 15 | solvent |
| Glycerol | 10 | solvent |
| Benzyl alcohol | 2 | solvent |
| Oleyl alcohol | 10 | solvent |
| Klucel ® | 0.75 | gelling agent |
| Propyl gallate | 0.05 | antioxidant |
| Ascorbyl palmitate | 0.02 | antioxidant |
| a-tocopherol | 0.002 | antioxidant |

Example 16

An exemplary anhydrous composition (NA 34) is described below:

| component | Wt % | Role |
| --- | --- | --- |
| Rapamycin | 3.2 | API |
| PEG400 | 51.7 | solvent |
| Propylene glycol | 1.5 | penetration enhancer/solvent |
| Transcutol P | 15 | Penetration enhancer/solvent |
| Diisopropyl adipate | 15 | solvent |
| Glycerol | 10 | solvent |
| Benzyl alcohol | 2 | solvent |
| Oleyl alcohol | 0.75 | solvent |
| Klucel ® | 0.75 | gelling agent |
| Propyl gallate | 0.05 | antioxidant |
| Ascorbyl palmitate | 0.02 | antioxidant |
| a-tocopherol | 0.002 | antioxidant |

Example 17

An exemplary ointment composition (O 11) is described below:

| component | Wt % | Role |
| --- | --- | --- |
| Rapamycin | 2.5 | API |
| PEG400 | 43 | solvent |
| Propylene glycol | 1.5 | penetration enhancer/solvent |
| Transcutol P | 29.45 | Penetration enhancer/solvent |
| Water | 7.8 | solvent |
| Benzyl alcohol | 2 | solvent |
| Oleyl alcohol | 0.75 | solvent |
| PEG 3350 | 13 | solvent |
| Propyl gallate | 0.05 | antioxidant |
| Ascorbyl palmitate | 0.02 | antioxidant |
| a-tocopherol | 0.002 | antioxidant |

Example 18

Ex Vivo Skin Permeation Experiment

Human donor skin was placed between upper and lower compartments. The lower compartment was filled with receiver fluid. Various rapamycin compositions were applied on the surface of the skin facing the upper compartment (11 formulations (i.e., O3, NA21, NA22, NA21, NA17, TD201, NA19, NA25, AG14, NA26 and NA24), n=6 replicates, dosage 10 mg/cm$^2$) and left for 24 hrs. A positive displacement pipette was used to apply the formulation (~10 mg/cm$^2$) to the plunger of a 1 mL syringe. The formulation (10+/−0.5 mg) was applied to the skin surface and spread over the diffusion area using the plunger. Prior to and after the application the weight of the plunger was recorded, from which the dose per cell was calculated.

Following the time period, the excess rapamycin compositions were wiped from the skin surface and the skin layers were separated into stratum corneum, epidermis, and dermis. The Stratum corneum was removed from the human skin using a tape stripping procedure. The epidermis was separated from the dermis by dry heating at 60° C. for 2 min. Rapamycin was extracted from each layer by 90:10 v/v ethanol:water solvent mixture, and quantified. The receiver fluid in the lower compartment was also analyzed for the presence of rapamycin.

As would be expected, the greatest amount of rapamycin was found on the surface of the skin after 24 hours. Further, there appeared to be more of the drug residing in the epidermis than either the stratum corneum or dermal layer. Furthermore, over time there was an increase in the amount of rapamycin quantified in both the epidermis and dermis. Rapamycin was not detected in the receiver fluid at any of the time points across the experimental period, suggesting that rapamycin did not fully pass through the skin layers.

Figure 2:
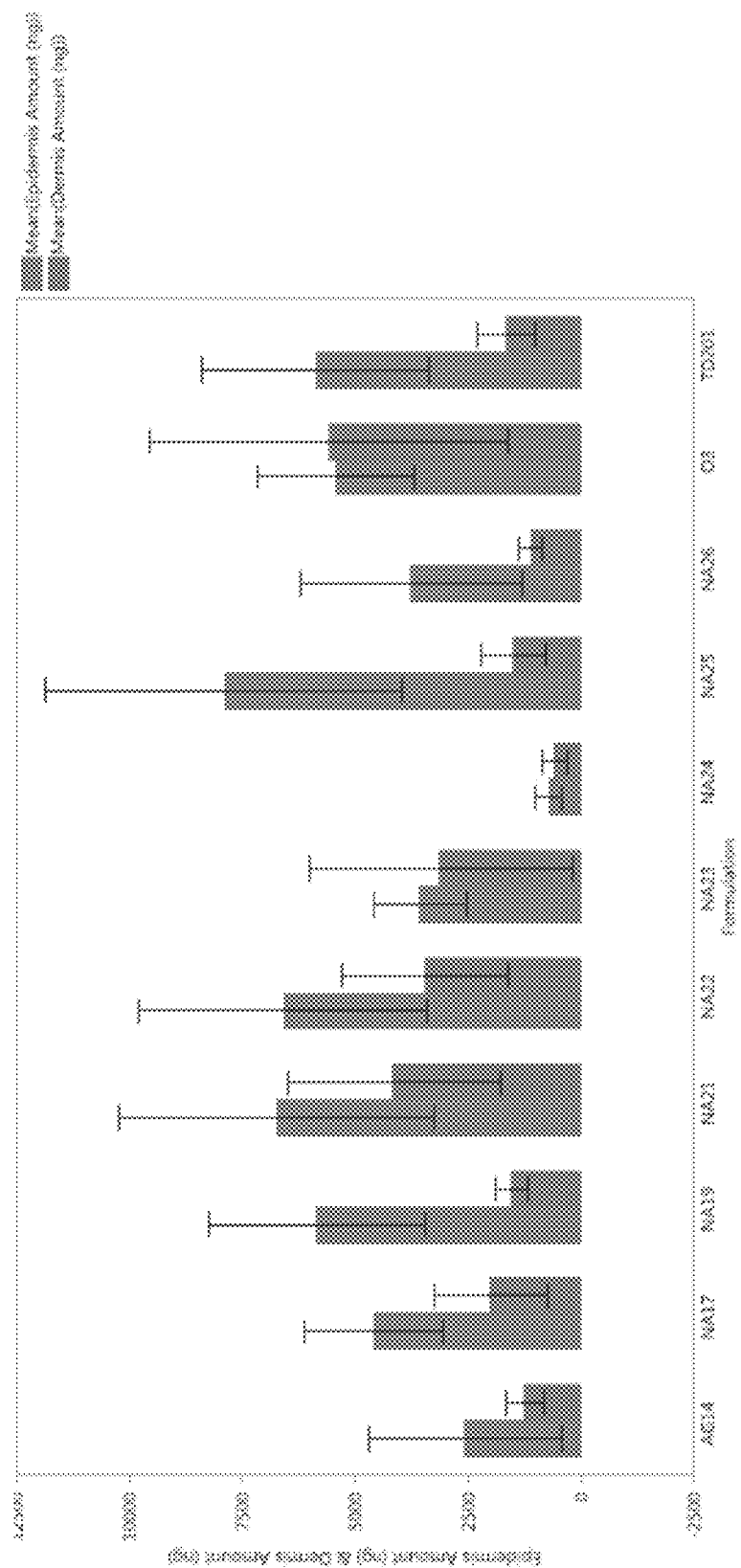
FIG. 2 depicts total mean amount of rapamycin (ng) recovered from epidermis and dermis, separately, following application of rapamycin compositions (O3, NA21, NA22, NA23, NA17, NA19, NA25, AG14, NA 26, NA24, TD201). Each error bar is determined using 1 standard deviation from the mean (n=5).

As shown in FIGS. 1 and 2, results from the penetration experiment revealed similarity of epidermal drug recoveries following application of all formulations when compared to TD201, with the exception of NA24, where amounts of drug recovered from the skin from TD201 were eightfold higher. Significantly higher amounts of drug in the dermis were observed from 03 when compared to TD201 (p<0.02), however all other formulations were statistically comparable but NA21, NA22 and NA23 exhibited higher average dermis levels than those observed in TD201. When delivery of the drug to the total tissue, i.e. the epidermis and dermis in combination was considered, all formulations exhibited drug recoveries statistically similar to TD201.

Figure 3:
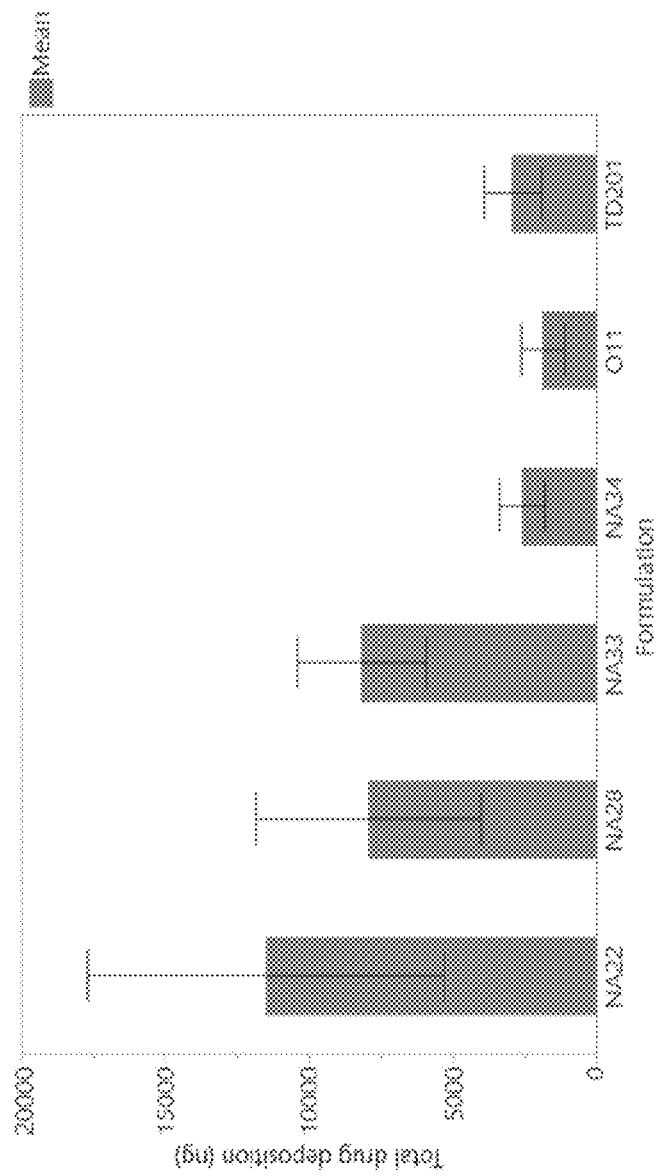
FIG. 3 depicts total mean deposition of rapamycin (ng) in the tissue (combined epidermis and dermis) following application of rapamycin compositions (NA22, NA28, NA33, NA34, O11, TD201). Each error bar is determined using 1 standard deviation from the mean (n=5).
Figure 4:
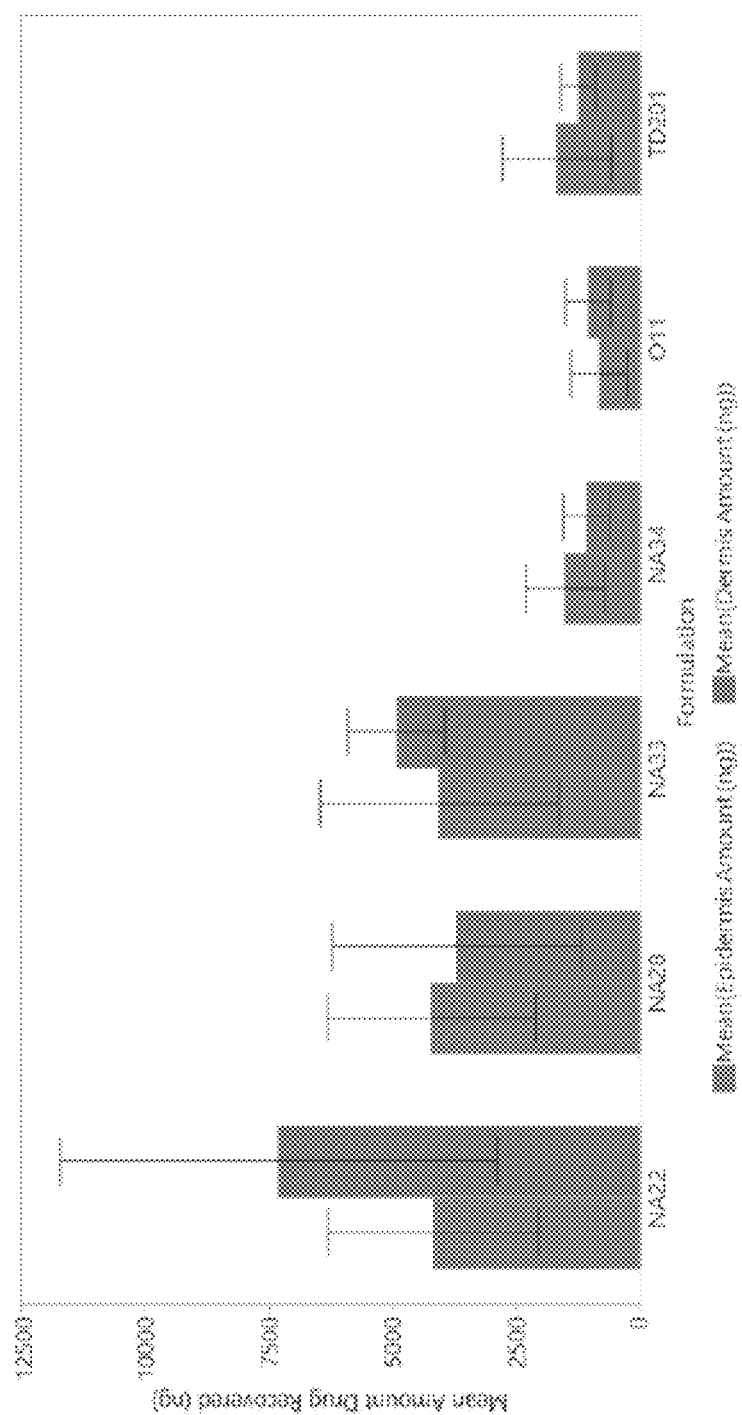
FIG. 4 depicts total mean amount of rapamycin (ng) recovered from epidermis and dermis, separately, following application of rapamycin compositions (NA22, NA28, NA33, NA34, O11, TD201). Each error bar is determined using 1 standard deviation from the mean (n=5).

Further, as shown in FIGS. 3 and 4, results of the penetration experiment indicated that significantly higher amounts of rapamycin were delivered to the epidermis following application of NA22, NA33 and NA28 when compared to 011 (p<0.05) while all other comparisons were statistically similar (i.e. TD201 performed similarly to all anhydrous formulations). Furthermore, NA22 was shown to outperform TD201, NA34 and 011 when levels of dermal drug delivery were considered, with significantly higher deposition in this skin layer than the aforementioned formulations (p<0.05). The results suggest that NA22 demonstrated enhanced drug delivery to the dermis and comparable delivery to the epidermis when compared to the formulation TD201.

In summary, anhydrous compositions showed significant amount of rapamycin deposition in the skin layers, when compared to aqueous compositions, AG14 and TD201.

Example 19: Evaluating Topical Bioavailability

Dermatopharmacokinetic (DPK) Studies

The dermatopharmacokinetic (DPK) approach is comparable to a blood, plasma, urine PK approach applied to the stratum corneum. DPK encompasses drug concentration measurements with respect to time and provides information on drug uptake, apparent steady-state levels, and drug elimination from the stratum corneum based on a stratum corneum concentration-time curve.

Application and Removal of Test and Reference Products: The treatment areas will be marked using a template without disturbing or injuring the stratum corneum/skin. The size of the treatment area will depend on multiple factors including drug strength, analytical sensitivity, the extent of drug diffusion, and exposure time. The stratum corneum is highly sensitive to certain environmental factors. To avoid bias and to remain within the limits of experimental convenience and accuracy, the treatment sites and arms will be randomized. Uptake, steady-state, and elimination phases, as described in more detail below, may be randomized between the right and left arms in a subject. Exposure time points in each phase may be randomized among various sites on each arm. The test and reference products for a particular exposure time point may be applied on sites to minimize differences. Test and reference products should be applied concurrently on the same subjects according to a SOP that has been previously developed and validated. The premarked sites will be treated with predetermined amounts of the products (e.g., 5 mg/sq cm) and covered with a nonocclusive guard. Occlusion will be used only if recommended in product labeling. Removal of the drug product will be performed according to SOPs at the designated time points, using multiple cotton swabs or Q-tips with care to avoid stratum corneum damage. In case of certain oily preparations such as ointments, washing the area with a mild soap may be needed before skin stripping. If washing is carried out, it will be part of an SOP.

Sites and Duration of Application: The bioavailability/bioequivalence (BA/BE) study will include measurements of drug uptake into the stratum corneum and drug elimination from skin. A minimum of eight sites will be employed to assess uptake/elimination from each product. The time to reach steady state in the stratum corneum will be used to determine timing of samples. For example, if the drug reaches steady-state in three hours, 0.25, 0.5, 1 and 3 hours posttreatment may be selected to determine uptake and 4, 6, 8 and 24 hours may be used to assess elimination. A zero time point (control site away from test sites) on each subject will be selected to provide baseline data. If the test/reference drug products are studied on both forearms, randomly selected sites on one arm may be designated to measure drug uptake/steady-state. Sites on the contralateral arm may then be designated to measure drug elimination. During drug uptake, both the excess drug removal and stratum corneum stripping times are the same so that the stratum corneum stripping immediately follows the removal of the excess drug. In the elimination phase, the excess drug will be removed from the sites at the steady-state time point, and the stratum corneum will be harvested at succeeding times over 24 hours to provide an estimate of an elimination phase.

Collection of Sample: Skin stripping proceeds first with the removal of the first 1-2 layers of stratum corneum with two adhesive tapes strip/disc applications, using a commercially available product (e.g., D-Squame, Transpore). These first two tape-strip(s) contain the generally unabsorbed, as opposed to penetrated or absorbed, drug and therefore will be analyzed separately from the rest of the tape-strips. The remaining stratum corneum layers from each site will be stripped at the designated time intervals. This is achieved by stripping the site with an additional 10 adhesive tape-strips. All ten tape strips obtained from a given time point will be combined and extracted, with drug content determined using a validated analytical method. The values will be generally expressed as amounts/area (e.g., ng/cm2) to maintain uniformity in reported values. Data may be computed to obtain full drug concentration-time profiles, Cmax-ss, Tmax-ss, and AUCs for the test and reference products.

Procedure for Skin Stripping:

To assess drug uptake: The test and/or reference drug products will be applied concurrently at multiple sites. After an appropriate interval, the excess drug from a specific site will be removed by wiping three times lightly with a tissue or cotton swab. Using information from the pilot study, the appropriate times of sample collection to assess drug uptake will be determined. The application of adhesive tape two times will be repeated, using uniform pressure, discarding these first two tape strips. Stripping will be continued at the same site to collect ten more stratum corneum samples. Care will be taken to avoid contamination with other sites. The procedure will be repeated for each site at other designated time points. The drug will be extracted from the combined ten skin strippings and the concentration will be determined using a validated analytical method. The results will be expressed as amount of drug per square cm treatment area of the adhesive tape.

To assess drug elimination: The test and reference drug product will be applied concurrently at multiple sites chosen based on the results of the pilot study. Sufficient exposure period to reach apparent steady-state level will be allowed. Excess drug from the skin surface will be removed as described previously, including the first two skin strippings. The skin stripping samples will be collected using ten successive tape strips at time intervals based on the pilot study and drug content will be analyzed.

Metrics and Statistical Analyses: A plot of stratum corneum drug concentration versus a time profile will be constructed to yield stratum corneum metrics of Cmax, Tmax and AUC. The two one-sided hypotheses at the $\alpha=0.05$ level of significance will be tested for AUC and Cmax by constructing the 90 percent confidence interval (CI) for the ratio between the test and reference averages. Individual subject parameters, as well as summary statistics (average, standard deviation, coefficient of variation, 90% CI) will be reported. For the test product to be BE, the 90 percent CI for the ratio of means (population geometric means based on log-transformed data) of test and reference treatments will fall within 80-125 percent for AUC and 70-143 percent for Cmax.

In Vivo Dermal Open Flow Microperfusion

In dermal open-flow microperfusion (dOFM), a thin, hollow tube will be inserted just under the skin surface, running through a section of the skin a few inches wide and then exiting. A liquid similar to body fluid will be injected into the tubing; a portion of the tube under the skin is porous, so any drug that has been applied and absorbed through the skin's outer layer enters the flowing liquid, which will be then collected for analysis. dOFM can reliably measure the changing amounts of drug in the skin after topical application of a dermatological drug product.

What is claimed is:

1. A topical anhydrous gel composition comprising:
   2.5 wt % to about 4.5 wt % of rapamycin or a pharmaceutically acceptable salt thereof, based upon the total weight of the composition,
   about 80 wt % to about 97 wt % of a solvent, based upon the total weight of the composition, wherein the solvent is about 1 wt % to about 30 wt % diisopropyl adipate based upon the total weight of the composition, about 1 wt % to about 30 wt % glycerol based upon the total weight of the composition, about 40 wt % to about 60 wt % polyethylene glycol based upon the total weight of the composition, and about 1 wt % to about 30 wt % isopropyl alcohol, based upon the total weight of the composition,
   about 0.1 wt % to about 5 wt % of a gelling agent, based upon the total weight of the composition,
   about 0.001 wt % to about 1 wt % of an antioxidant, based upon the total weight of the composition, and
   optionally an additional pharmaceutically acceptable excipient,
   wherein a total weight of the composition is 100 wt %, and
   wherein the anhydrous gel composition has a pH of about 4 to about 6.

2. The topical anhydrous gel composition of claim 1, wherein the gelling agent is selected from the group consisting of hydroxypropyl cellulose, carbomer 981, carbomer 934P, glyceryl tris 12-hydroxy stearate, hydroxy stearin, propylene carbonate, polyvinyl pyrrolidine, and combinations thereof.

3. The topical anhydrous gel composition of claim 1, wherein the antioxidant is selected from the group consisting of ascorbyl palmitate, propyl gallate, α-tocopherol, and combinations thereof.

4. The topical anhydrous gel composition of claim 1, wherein the composition further comprises a polymeric surfactant, a moisturizing agent, a cooling agent, a rheology modifier, a preservative, and combinations thereof.

5. The topical anhydrous gel composition of claim 1, wherein the composition further comprises a skin care agent selected from the group consisting of cis- retinoic acid, trans-retinoic acid, retinol, retinyl esters, and combination thereof.

6. The topical anhydrous gel composition of claim 1, wherein the composition comprises:
   rapamycin from about 3 wt % to about 4.5 wt % of the composition;
   polyethylene glycol from about 40 wt % to about 60 wt % of the composition;
   isopropyl alcohol at about 15 wt % of the composition;
   diisopropyl adipate at about 15 wt % of the composition;
   glycerol at about 10 wt % of the composition;
   the gelling agent from about 0.1 wt % to about 1 wt % of the composition;
   the antioxidant from about 0.001 wt % to about 0.1 wt % of the composition; and
   wherein the additional pharmaceutically acceptable excipient is a buffer.

7. The topical anhydrous gel composition of claim 6, wherein the composition comprises:
   rapamycin at about 3.9 wt % of the composition;
   isopropyl alcohol at about 15 wt % of the composition;
   polyethylene glycol at about 55.3 wt % of the composition;
   diisopropyl adipate at about 15 wt % of the composition;
   glycerol at about 10 wt % of the composition;
   wherein the gelling agent is hydroxypropyl cellulose;
   wherein the antioxidant is selected from propyl gallate, ascorbyl palmitate, and alpha-tocopherol; and
   a buffer.

8. The topical anhydrous gel composition of claim 7, wherein the anhydrous gel composition comprises:
   rapamycin at about 3.9 wt % of the composition;
   isopropyl alcohol at about 15 wt % of the composition;
   polyethylene glycol at about 55.3 wt % of the composition;
   diisopropyl adipate at about 15 wt % of the composition;
   glycerol at about 10 wt % of the composition;
   hydroxypropyl cellulose at about 0.75 wt % of the composition;
   propyl gallate at about 0.05 wt % of the composition;
   ascorbyl palmitate at about 0.02 wt % of the composition;
   alpha-tocopherol at about 0.002 wt % of the composition; and
   a buffer.

9. The topical anhydrous gel composition of claim 1, wherein the composition has a pH of about 4.5 to about 5.

10. The topical anhydrous gel composition of claim 1, wherein the composition has a viscosity of about 5000 cP to about 20,000 cP.

11. The topical anhydrous gel composition of claim 1, wherein the rapamycin or pharmaceutically acceptable salt thereof is stable in the composition at a temperature of about 4° C. to about 40° C. for a period of 12 to 36 months.

* * * * *